US009168281B2

(12) United States Patent
Worden, Sr.

(10) Patent No.: US 9,168,281 B2
(45) Date of Patent: Oct. 27, 2015

(54) KIT FOR TREATING A WOUND

(76) Inventor: Charles E. Worden, Sr., Fort Wayne, IN (US)

(*) Notice: Subject to any disclaimer, the term of this patent is extended or adjusted under 35 U.S.C. 154(b) by 90 days.

(21) Appl. No.: 13/417,012

(22) Filed: Mar. 9, 2012

(65) Prior Publication Data

US 2012/0230968 A1 Sep. 13, 2012

Related U.S. Application Data

(60) Provisional application No. 61/451,093, filed on Mar. 9, 2011.

(51) Int. Cl.
A61K 35/19 (2015.01)
A61K 36/886 (2006.01)
A61K 39/395 (2006.01)
C07K 16/00 (2006.01)
A61K 31/355 (2006.01)
A61K 31/375 (2006.01)
A61K 31/4425 (2006.01)
A61K 31/07 (2006.01)

(52) U.S. Cl.
CPC ............... A61K 36/886 (2013.01); A61K 31/07 (2013.01); A61K 31/355 (2013.01); A61K 31/375 (2013.01); A61K 31/4425 (2013.01); A61K 35/19 (2013.01); A61K 39/395 (2013.01); C07K 16/00 (2013.01)

(58) Field of Classification Search
CPC ............ A61K 48/0033; A61K 48/005; A61K 48/0066; A61K 9/1271; A61K 31/7088; A61K 31/7105; A61K 38/4833; A61K 48/00; A61K 48/0041; A61K 9/0019; A61K 9/0024; A61K 9/0048; A61K 9/1272; A61K 9/14; A61K 9/16; A61K 2300/00; A61K 31/07; A61K 31/355; A61K 31/375; A61K 31/4425; A61K 35/19; A61K 36/886; A61K 39/395; A61K 31/27; A61K 31/428; A61K 31/554; A61K 8/046; A61K 8/39; A61K 8/731; A61K 8/86; A61K 9/004; C07K 16/00
See application file for complete search history.

(56) References Cited

U.S. PATENT DOCUMENTS

| | | | |
|---|---|---|---|
| 4,059,967 A | 11/1977 | Rowe et al. | |
| RE32,874 E | 2/1989 | Rock et al. | |
| 5,165,938 A * | 11/1992 | Knighton | 424/532 |
| 5,378,601 A | 1/1995 | Gepner-Puszkin | |
| 5,470,831 A | 11/1995 | Whitman et al. | |
| 5,776,892 A | 7/1998 | Counts et al. | |
| 5,981,606 A | 11/1999 | Martin | |
| 6,303,112 B1 | 10/2001 | Worden | |
| 6,524,568 B2 | 2/2003 | Worden | |
| 7,112,342 B2 | 9/2006 | Worden | |
| 2003/0007957 A1 | 1/2003 | Britton et al. | |
| 2003/0152639 A1 | 8/2003 | Britton et al. | |
| 2006/0240116 A1 | 10/2006 | Jolley | |
| 2009/0035289 A1 | 2/2009 | Wagner et al. | |
| 2010/0226902 A1 | 9/2010 | Fylling | |

OTHER PUBLICATIONS

Lacerum® Wound Cleanser. Charles E. Worden, BeluMed X, LLC. Feb. 24, 2004 [retrieved on Apr. 26, 2012]. Retrieved from the Internet: <URL:http://www.agrilabs.com/documents/Lacerum%20Wound%20Cleanser.pdf>, p. 1-7.
PRP: Platelet Rich Plasma. Wes Sutter, DVM, ACVS. Oct. 2007 [retrieved on Apr. 24, 2012]. Retrieved from the Internet: URL:http://www.vetstem.com/pdfs/sutter.pdf>, p. 1-8.
Wounds Respond to Well-Horse. Medicine Chet in Horse Journal, 2009, vol. 16, No. 10, p. 10-12.
PCT International Search Report and Written Opinion dated May 17, 2012, for PCT application No. PCT/US2012/028602.
Response to Final Office Action, filed Nov. 13, 2009, in U.S. Appl. No. 11/112,968.

* cited by examiner

Primary Examiner — Debbie K Ware
(74) Attorney, Agent, or Firm — Mintz Levin Cohn Ferris Glovsky and Popeo, P.C.

(57) ABSTRACT

Provided herein are compositions for treating wounds, method of making and using the system thereof. The system or kit for treating a wound includes a first composition having cetylpyridinium chloride, Aloe vera, and ascorbic acid for sanitizing a wound. The system or kit includes a second composition having concentrated platelet-rich plasma and a hypertonic saline solution for activating granulation of the wound. The system or kit includes a third composition having Aloe vera, ascorbic acid, vitamin A, vitamin E and immunoglobulins for initiating re-epithelialization of the wound.

27 Claims, No Drawings

KIT FOR TREATING A WOUND

REFERENCE TO PRIORITY DOCUMENT

This application claims priority of U.S. Provisional Patent Application Ser. No. 61/451,093, filed Mar. 9, 2011. The disclosure of the provisional patent application is hereby incorporated by reference in its entirety.

BACKGROUND

There have been a variety of substances and methods developed in the past for treating wounds, depending upon the type and location and severity of the wound. Topical antiseptics which contain toxic metal iodine as the active ingredient, such as povidone-iodine (PVPI) and other tinctures of this metal, are known and frequently used, for example in veterinary medicine for lacerations in horses, to prevent infections by sterilizing the wound and skin surface. These heavy metal disinfectants although effective as an anti-microbial can be toxic to living tissues and detrimental to the wound healing process.

There is a need for more effective approaches to treating chronic wounds that promote tissue regeneration and avoid furthering tissue damage. Therefore, it is an object herein to provide such treatments.

SUMMARY

Provided herein are compositions for treating wounds, a method of making the compositions and use of the treatment system thereof.

In one aspect, provided is a system for treating a wound. This system includes a first composition having cetylpyridinium chloride, Aloe vera, and ascorbic acid for sanitizing a wound. The system includes a second composition having concentrated platelet-rich plasma and a hypertonic saline solution for activating granulation of the wound. The system includes a third composition having Aloe vera, ascorbic acid, vitamin A, vitamin E and immunoglobulins for initiating re-epithelialization of the wound.

The first composition can be in the liquid form. The liquid can be a shampoo, pump spray, or an aerosol spray. The second composition can be in a fresh frozen or freeze-dried form. The second composition can further include a platelet activator. The second composition can activate granulation of the wound up to a level of a skin surface surrounding the wound. The third composition can be in a gel or solid form. The third composition can be applied using a squeeze tube or stick. The third composition can avoid altering natural hair color at and around the wound. The third composition can accelerate migration across the wound, wound contraction, and keep the wound moist.

The wound can be on a mammal and the mammal can be a primate or a non-primate. The concentrated platelet-rich plasma can be prepared from autologous blood. The concentrated platelet-rich plasma can be prepared from heterologous blood. The wound can be on a mammal, and the heterologous blood can be from a species other than the species of the mammal. The wound can be an injury of a bodily tissue including skin, muscle, bone, cartilage, collagen, connective tissue, adipose, mucus membrane, cornea, ear and other tissues and parts of the body. The injury can be a puncture, laceration, surgical incision, chronic wound, pressure wound, open abscess, sacral lick, granuloma, abrasion, burn, chronic would, otitis, corneal ulcer, ear infection, snake bite or spider bite. The wound can be a chronic wound of an equine lower limb.

The system can further include a wound cover. The first, second and third compositions can be applied separately and sequentially. The first composition can be applied prior to the second composition and the second composition can be applied prior to the third composition. The first composition can be applied one or more times a day for at least 5 days. The second composition can be applied until granulation of the wound is up to the level of a skin surface surrounding the wound. The third composition can be applied once an epithelial border of the wound forms.

In an interrelated aspect, disclosed is a method of treating a wound in a mammal. The method includes sanitizing a wound in a mammal by flushing the wound with a first composition including cetylpyridinium chloride, Aloe vera, and ascorbic acid. The sanitizing is performed one or more times a day for at least 5 days. The method includes activating granulation of the wound by spraying the wound with a second composition including concentrated platelet-rich plasma and a hypertonic saline solution. The method includes initiating re-epithelialization of the wound by coating the wound with a third composition including Aloe vera, ascorbic acid, vitamin A, vitamin E and immunoglobulins.

In an interrelated aspect, disclosed is a method of treating a wound including sanitizing a wound by flushing the wound with a first composition including cetylpyridinium chloride, Aloe vera, and ascorbic acid. The method includes activating granulation of the wound by spraying the wound with a second composition including concentrated platelet-rich plasma and a hypertonic saline solution. The method includes initiating re-epithelialization of the wound by coating the wound with a third composition including Aloe vera, ascorbic acid, vitamin A, vitamin E and immunoglobulins.

The first composition can be in the liquid form. The liquid can be a shampoo, pump spray, or an aerosol spray. The second composition can be in a fresh frozen or freeze-dried form. The second composition can further include a platelet activator. The second composition can activate granulation of the wound up to the level of a skin surface surrounding the wound. The third composition can be in a gel or solid form. The third composition can be applied using a squeeze tube or stick. The third composition can avoid altering natural hair color at and around the wound. The third composition can accelerate migration across the wound, wound contraction, and keep the wound moist.

The wound can be on a mammal, and the mammal can be a primate or a non-primate. The concentrated platelet-rich plasma can be prepared from autologous blood. The concentrated platelet-rich plasma can be prepared from heterologous blood. The wound can be on a mammal, and the heterologous blood can be from a species other than the species of the mammal. The wound can be an injury of a bodily tissue including skin, muscle, bone, cartilage, collagen, connective tissue, adipose, mucus membrane, cornea, ear and other tissues and parts of the body. The injury can be a puncture, laceration, surgical incision, chronic wound, pressure wound, open abscess, sacral lick, granuloma, abrasion, burn, chronic would, otitis, corneal ulcer, ear infection, snake bite or spider bite. The wound can be a chronic wound of an equine lower limb. The wound can be covered during one or more portions of the method. The sanitizing, activating and initiating portions of the method can be performed separately and sequentially. The sanitizing portion can be performed prior to the activating portion and the activating portion can be performed prior to the initiating portion of the method. The sanitizing portion of the method can be performed one or more times a day for at least 5 days. The activating portion of the method can be performed until granulation of the wound is up to the level of a skin surface surrounding the wound. The initiating portion of the method can be performed once an epithelial border of the wound forms.

More details of the compositions, methods and system of use are set forth in the accompanying drawings and the description below. Other features and advantages will be apparent from the description and drawings.

DETAILED DESCRIPTION

Provided herein are compositions and systems for treating wounds, a method of making and use of the compositions and systems thereof. A wound is generally defined as an injury to an area of the body of a human or animal. Medical practice characterizes wounds as chronic or acute, according to the persistence and severity of the wound. A chronic wound is one that is prolonged or lingering, rather than promptly healed. An acute wound is one that occurs relatively quickly, and heals relatively quickly as well. Tissue wounds may have a wide spectrum of manifestations, as small as merely an abnormal microscopic tear or fissure in tissue (or a surface thereof), or as large as the abrasion or ablation of the skin covering a substantial portion of the body, such as in a burn victim.

Wound healing progresses through a series of processes, which include the formation of granulation tissue, epithelialization and connective tissue remodeling. These events involve continuous modification of the complex cellular support matrix such as by matrix metalloproteinases (MMPs) in support of wound healing, morphogenesis, tissue resorption and remodeling, as well as nerve growth and hair follicle development. Platelets also perform many functions in wound healing such as plugging leaks in blood vessels and helping begin the process leading to the formation of a blood clot. Activation of a platelet by an agonist such as thrombin, or other agonists such as those listed elsewhere herein, leads to granulation activation and the release of protein growth factors. These released growth factors are important in angiogenesis and stimulate the formation of new tissue.

I. DEFINITIONS

As used herein, the term "wound" may mean an injury of a bodily tissue including, but not limited to, skin, muscle, bone, cartilage, collagen, connective tissue, adipose, mucus membrane, cornea, ear and other tissues and parts of the body.

As used herein, a "subject" or "patient" may mean any animal or mammal, including humans and non-human primates as well as non-primates such as horses, cows, and other livestock, as well as dogs, cats and other domesticated companion animals.

As used herein, "treatment" or "therapy" may mean any manner in which a symptom of a wound condition, disorder or disease are ameliorated or otherwise beneficially altered. Treatment also encompasses use of the compositions described herein.

As used herein, "therapeutically effective amount" may mean the amount or amounts of the constituent elements or combination thereof necessary to promote or enhance treatment such as, for example, in the context of wound healing including the reduction in the volume or surface area of a wound, the increase in the amount of granulation tissue or other biological material facilitating collagen lay-down, vascular in-growth, fibroblast proliferation or overall healing.

As used herein, the term "growth factor" may mean any biological material(s) promoting tissue or cell growth.

As used herein, "platelet activation" may mean an agonist event, either a biochemical or mechanically induced event that causes a platelet to degranulate and the platelet cell wall to rupture. Activation would include mechanical activation such as freezing and physically rupturing the platelet walls to release the granules. Activation would also include, without limitation biochemical activation using thrombin, including native thrombin, calcified thrombin, bovine thrombin (such as AUTOLOGEL), autologous thrombin, allogeneic thrombin, or recombinant human thrombin, tissue factor, von Willebrand factor, platelet factor 4, collagen, thromboxane A2, serotonin, adenosine diphosphate (ADP) and acetylcholine (ACH).

As used herein, "autologous" may mean collection of a component from the wounded's own biological material. "Heterologous" may mean the collection of biological materials obtained from one or more third parties that need not be of the same species as the patient whose wound is being treated. It should be appreciated that the biological material specified herein can originate from a patient being treated, from a single third party, or from a plurality of third parties. The third parties can be of the same species as the patient being treated or of another species, so long as the wound treatment material derived from such biological materials is biocompatible with the patient. As another example, when the description identifies a particular substance, it is sufficient to use any form of that substance having the characteristic(s) needed to satisfy the stated need; for instance, unless the context indicates otherwise, a need for growth factors may be satisfied by providing isolated growth factors or those that are included in platelets or other types of cells, and/or combinations thereof. Similarly, the process deployed to obtain the growth factors may be any process that satisfactorily does so, regardless of whether it includes centrifugation.

As used herein, "anti-oxidant" or "free radical scavenger" may mean any material(s) having anti-oxidant properties. Anti-oxidant would include, without limitation, vitamins such as vitamins A, C (ascorbic acid) and E and non-vitamins such as beta carotene or any retinoid.

II. THERAPEUTIC AGENTS

In the most general terms, described herein are compositions and systems and methods of using the compositions for the treatment of wounds. These wounds may be surgically induced, from bites, punctures, or of a chronic nature, which are wounds that are difficult to heal, or a wound in which it would be desirable to have a more cosmetic heal. It should be appreciated that the compositions described herein can include one or more of a variety of agents that can be used individually or in combination on the wound, for example, an anti-oxidant, antiseptic, *Aloe vera*, a growth factor, such as a platelet-derived growth factor or immunoglobulin. The compositions can be used in one or more combinations with one another and in one or more routes of administration to create a complete wound care system.

The compositions described herein can include one or more anti-oxidants or free radical scavengers to help minimize free radical damage and promote more rapid healing. When living tissue uses oxygen at the cellular level, unstable molecules termed free radicals are generated. Free radicals can include reactive oxygen species such as super-oxidants and hydrogen peroxide ($H_2O_2$) and reactive nitrogen species such as nitric oxide and peroxynitrites. Free radicals are unstable oxygen molecules that cause damage to cellular components such as DNA, proteins, or lipids and can induce cell death. The body naturally generates free radicals, which are generally neutralized in vivo by biochemical reactions. The concentration of free radicals is extremely high in a wound bed due to damage to the cells in wounded tissue. Immune cells migrating into the wound bed can induce inflammation and release more free radicals that do further damage to nearby cells. Inflammation can be directly proportional to the amount of scarring that can occur.

The anti-oxidants provided in the compositions described herein can include, but not limited to, vitamins such as vitamin C (ascorbic acid), vitamin E, vitamin A and other retinoids; and the carotenes such as β-carotene. In addition to its anti-oxidant functions, ascorbic acid can stimulate and organize the wound healing process due to its stimulatory effects on collagen production. Collagen can provide strength and structure to skin, cartilage and bone, and is the scaffold upon which the regenerated cellular and non-cellular elements of the wound can attach and grow. Ascorbic acid is known to have preservative properties, unless it is broken down such as occurs after exposure to sunlight or another source of ultraviolet (UV) light. Vitamin E is also known to break down upon exposure to sunlight or UV light. As such, coverings can be used to shield the components of the compositions from UV rays upon application.

The compositions described herein can also include one or more antiseptic, anti-infective, antibiotic, bacteriocidal, antifungal, anti-microbial agent or another agent that sanitizes the wound. Many wound sites are either already infected with bacteria or are susceptible to such infection. As such it is desirable that the composition be capable of either killing bacteria or preventing the mobility or the reproduction of bacteria already present in a wound. In an embodiment the antiseptic agent includes, but is not limited to, cetylpyridinium chloride (CPC) and other quaternary ammonium compounds or a combination thereof. In an embodiment, the composition includes an agent that is bacteriocidal to at least the *Pseudomonas* and *Klebsiella* genera of bacteria. The agent can be effective against *E. coli*, species of *Streptococcus, Shigella, Salmonella* and most species of *Staphylococcus* including *S. aureus* and MRSA as well. The agent can include neosporin, vancomycin and gentamycin, and combinations thereof.

The compositions described herein can include one or more plant components or plant extracts including, but not limited to, *Aloe vera*. The *Aloe vera* contained in the compositions described herein is generally a high quality, whole leaf *Aloe vera* gel that is in the range of 40:1 or greater. In an embodiment, the compositions described herein include at least 200:1 whole leaf *Aloe vera*.

The compositions described herein can also include one or more growth factors, cytokines or chemokines. In an embodiment, the growth factors for use can include platelet-derived growth factor (PDGF), platelet-derived angiogenesis factor (PDAF), vascular endothelial growth factor (VEGF), platelet-derived epidermal growth factor (PDEGF), platelet factor 4 (PF-4), transforming growth factor β (TGF-β), acidic fibroblast growth factor (FGF-A), basic fibroblast growth factor (FGF-B), transforming growth factor a (TGF-A), insulin-like growth factors 1 and 2 (IGF-1 and IGF-2), β thromboglobulin-related proteins (β TG), thrombospondin (TSP), fibronectin, von Wallebrand factor (vWF), fibropeptide A, fibrinogen, albumin, plasminogen activator inhibitor 1 (PAI-1), osteonectin, regulated upon activation normal T cell expressed and presumably secreted (RANTES), gro-α, vitronectin, fibrin D-dimer, factor V, antithrombin ID, immunoglobulin-G (IgG), immunoglobulin-M (IgM), immunoglobulin-A (IgA), a2-macroglobulin, angiogenin, Fg-D, elastase, keratinocyte growth factor (KGF), epidermal growth factor (EGF), fibroblast growth factor (FGF), tumor necrosis factor (TNF), fibroblast growth factor (FGF) and interleukin-1 (IL-1), Keratinocyte Growth Factor-2 (KGF-2) and combinations thereof. Each of these growth factors is known or believed to enhance cell or tissue growth. Moreover, said substances, or various combinations thereof, are known or believed to function together in an unexpected synergistic manner to promote wound healing. It should be appreciated that the growth factors can be derived from activated platelets, cultured cells, or from protein expression systems.

The compositions described herein can include concentrated platelets, or platelet rich plasma (PRP) as the growth factor source. The platelets can be separated from the red blood cells and white blood cells of whole blood, primarily through differential centrifugation, although any suitable method for separating platelets from whole blood may be employed. Incidental amounts of white blood cells can be present due to the fact that the platelets are rarely totally isolated from the other blood components. In an embodiment, the range of the mean platelet volume of the platelets being sequestered is in the range of about 6.6 to 8.4 femtoliters, with an average of about 7.7 femtoliters. In another embodiment, the range of the mean platelet volume of the platelets being sequestered is in the range of about $250 \times 10^{11}$ per cc blood or greater. In another embodiment, the range of the mean platelet volume of the platelets being sequestered is in the range of about $450 \times 10^{11}$ per cc blood. The concentrated platelets or PRP can be frozen or freeze-dried as will be described in more detail below.

Some of the compositions described herein can include one or more biochemical platelet activators or agonists including, but not limited to, thrombin, including native thrombin, calcified thrombin, bovine thrombin (such as in AUTOLOGEL®), autologous thrombin, allogeneic thrombin, or recombinant human thrombin, tissue factor, von Willebrand factor, platelet factor 4, collagen, thromboxane A2, serotonin, adenosine diphosphate (ADP), acetylcholine (ACH), or combinations thereof to activate the platelets to release the contents of their stored granules into the plasma. Activators and agonists can be mixed with the plasma-containing compositions immediately prior to application to a patient. In addition, the compositions described herein can include one or more activator co factors including, but not limited to divalent cations such as calcium ions, sodium ions, calcium salts in order to implement the clotting cascade and activate platelets to release the alpha granules. Suitable calcium salts include, without limitation, $CaCO_3$, $CaSO_4$, $CaCl_2$, $CaCl_2$ which can be available as calcium chloride injection, USP 10% (AMERICAN REGENT® Laboratories, Inc., Shirley, N.Y., USA).

III. FORMULATIONS AND PREPARATION OF COMPOSITIONS

Pharmaceutical carriers or vehicles suitable for administration of the compositions described herein and for the methods provided herein include any such carriers known to those skilled in the art to be suitable for the particular mode of administration. In addition, the compounds can be formulated as the sole active ingredient in the composition or may be combined with other active ingredients.

The active ingredient may be administered at once, or may be divided into a number of smaller doses to be administered at intervals of time. It is understood that the precise dosage and duration of treatment is a function of the tissue being treated and may be determined empirically using known testing protocols or by extrapolation from in vivo or in vitro test data. It is to be noted that concentrations and dosage values may also vary with the age of the individual treated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

The resulting mixtures may be solutions, suspensions, emulsions or the like and can be formulated as aqueous mixtures, creams, gels, ointments, emulsions, solutions, elixirs, lotions, shampoos, suspensions, tinctures, pastes, foams, aerosols, irrigations, sprays, bandages, or any other formulation suitable for topical or local administration.

Pharmaceutical and cosmetic carriers or vehicles suitable for administration of the compounds provided herein include any such carriers known to those skilled in the art to be suitable for the particular mode of administration. In addition, the compounds may be formulated as the sole active ingredient in the composition or may be combined with other active ingredients. The active compound is included in the carrier in an amount sufficient to exert a therapeutically useful effect in the absence of serious toxic effects on the treated individual. The effective concentration may be determined empirically by testing the compounds using in vitro and in vivo systems.

Solutions or suspensions used for local application can include any of the following components: a sterile diluent, such as water, saline solution, fixed oil, polyethylene glycol, glycerin, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity such as sodium chloride or dextrose. Liquid preparations can be enclosed in ampoules, or multiple dose vials made of glass, plastic or other suitable material. Suitable carriers may include physiological saline or phosphate buffered saline (PBS), and the suspensions and solutions may contain thickening and solubilizing agents, such as glucose, polyethylene glycol, and polypropylene glycol and mixtures thereof. These may be prepared according to methods known to those skilled in the art.

The composition provided herein can further contain one or more adjuvants that facilitate delivery, such as, but are not limited to, inert carriers, or colloidal dispersion systems. Representative and non-limiting examples of such inert carriers can be selected from water, isopropyl alcohol, gaseous fluorocarbons, ethyl alcohol, polyvinyl pyrrolidone, propylene glycol, a gel-producing material, stearyl alcohol, stearic acid, spermaceti, sorbitan monooleate, methylcellulose, as well as suitable combinations of two or more thereof.

Finally, the compounds may be packaged as articles of manufacture containing packaging material, one or more therapies as provided herein within the packaging material, and a label that indicates the indication for which the therapy is provided.

A. Wound Sanitizer

One embodiment of the composition can be a tissue-friendly wash or rinse or spray that can be used to clean and sanitize the wound site prior to or in coordination with further treatments. This embodiment is gentle and allows for new cells to proliferate and migrate within the wound bed compared to other more caustic products currently known. The composition can be manufactured as a liquid that can flush a wound such as a chronic skin wound, corneal ulcer or other eye injury, or an ear injury. In an embodiment, the composition can be manufactured as a shampoo. The composition can be packaged such that it can be sprayed onto a wound surface using a pump spray or an aerosol spray. It should be appreciated that the composition can also be packaged in another form such as a thickened gel or suppository that can be inserted into a deep puncture wound such as a stab or gunshot wound.

The composition can include cetylpyridinium chloride (CPC), Aloe vera and ascorbic acid. The composition can include at least about 0.04% CPC to at least about 0.2% CPC. The Aloe vera (ALOECORP®, Inc. Lacey, Wash.) can be at least about 40:1 to about 200:1 W.L. per US 1 gal. The Aloe vera can be a dissolvable dehydrated flake that can be added to distilled water to become a liquid base. The ascorbic acid can be at least about 20 g USP per US 1 gal. The composition can include other non-active ingredients such as glycerol and anti foam agents. Table 1 shows an example of a formula for the wound sanitizer.

TABLE 1

Wound Sanitizer with Aloe Vera and ascorbic acid

| | |
|---|---|
| cetyl pyridinium chloride | 12 mL |
| Aloe Vera W.L. (200:1) | 20 g |
| Glycerol USP | 5 mL |
| Ascorbic Acid USP | 20 g |
| Anti-Foam | 0.4 mL |
| Deionized water | Bring up to 1 Gal |

Allow to stand 10 Minutes

B. Tissue Regenerator

Another embodiment of the composition can be used to accelerate both angiogenesis and re-epithelialization in tissue regeneration. The composition can reduce scarring by reducing inflammation and help to eliminate infection by the rapid regeneration of granulation tissue up to skin level. The composition can be manufactured as a fresh frozen or freeze-dried form such that it can be sprayed onto a wound bed, such as using a pump spray or an aerosol spray. The composition can also be poured or applied via an impregnated bandage onto a wound.

The composition can include concentrated platelet-rich plasma (PRP), and optionally a platelet activator. The PRP can be prepared from whole blood, which can be spun down slowly or allowed to settle out at room temperature without the help or benefit of centrifugation until the cellular portions separate. The whole blood can be autologous or heterologous blood obtained from an approved blood source. The PRP obtained can be species-specific. In an embodiment, the PRP can be obtained from whole blood of equines, canines or felines. The PRP can be retained for processing and the red cells discarded or returned to the patient.

In an embodiment, the plasma is prepared in a freeze-dried, concentrated platelet-rich plasma (PRP) solution that can be applied topically to a wound bed. In this embodiment, freezing activates the platelets and no external activator agent is necessary. It should be appreciated that the plasma can also prepared in a fresh, frozen state and optionally an activator and activator co-factor included, if deemed necessary. The PRP can be freeze-dried in order to keep viable the growth factors and enzymes released into the plasma upon platelet activation. Freezing can activate the platelets as well as further disrupt the platelet walls.

In one embodiment, the PRP can be combined with a hypertonic saline solution, for example 250 mL of 2.0% saline solution can be added to 1,000 mL of the PRP, prior to freezing to disrupt the platelet wall. It should be appreciated that a higher concentration of saline solution could also be used such as 2.5%, 3.0% or higher. The resulting fluid, or growth factor soup (GFS) can be divided into aliquots in 20 ml glass vials and moved to the dryer trays in order to freeze-dry the GFS. The temperature can be lowered slowly to minus 30° F. over a period of six to eight hours. The freeze period should generally not exceed eight hours. After the freeze is complete, the drying process starts using a vacuum pump and a heating shelf. Vacuum pump pressure should generally not exceed 240 mm Torr and dry time should generally not exceed 48 hours. A freeze-dried platelets or GFS can be more easily shipped and has a longer shelf life than fresh frozen platelets or GFS.

C. Finishing Composition

Another embodiment of the composition can be used as a final step in providing a complete cosmetic healing of a wound. The composition can be used to reduce inflammation, speed healing time and increase tensile strength of the healed wound. This composition can accelerate migration of cells across the wound bed and help to keep the wound moist. It can provide cosmetic healing properties, for example, maintaining natural hair color at the wound site. The composition can be manufactured as an *Aloe vera* based cream or paste that can be applied to the epithelial borders of a wound such as using a squeeze tube or stick.

The composition can include an *Aloe vera* gel 200:1 whole leaf, and other anti-oxidant vitamins, such as ascorbic acid, Vitamin A, and Vitamin E, as well as immunoglobulins and/or serum albumin. The immunoglobulins can be equine immunoglobulin such as IgG, IgE, IgA, IgD, and IgM.

In one embodiment, the composition can include a hydrogel and *Aloe vera* W.L. 200:1 gel base including vitamin A lipomicron and vitamin E lipomicron. The hydrogel and *Aloe vera* stock can be used to formulate the remainder of the composition including (per 5 US Gallons) 200 mL of ascorbic acid solution (50 g in 200 mL deionized water); 200 mL of 0.04% CPC, 1,000 mL of plasma or another source of immunoglobulins. Optionally, 1,000 units of bovine thrombin rehydrated with CaCl can be included. Tables 2 and 3 show examples of formulas for the finishing composition.

TABLE 2

Aloe Vera Aqua Gel Base formula for finishing composition:

| | |
|---|---|
| Mineral Oil | 0.050 |
| Stearic acid | 0.025 |
| GMS | 0.010 |
| Cetyl Alcohol | 0.100 |
| Silicone 350 | 0.002 |
| Propylparaben | 0.001 |
| Glycerin | 0.070 |
| Trolamine | 0.010 |
| Germall | 0.005 |
| Methylparaben | 0.002 |
| Carbomer 934 | 0.001 |
| Shea Butter | 0.030 |
| Aloe Vera | 0.050 |
| Vitamin A Lipomicron | 0.003 |
| Vitamin E Lipomicron | 0.003 |
| Water | 0.638 |
| Aqua Gel Base Total | 1.000 |
| CPC (0.04%) | 200 ml |
| Equine Plasma | 1000 ml |
| Vitamin C solution | 50 ml |
| Glycerol | 150 ml |

TABLE 3

Aloe Vera Aqua Gel Base formula for finishing composition:

| | |
|---|---|
| Mineral Oil | 0.050 |
| Stearic acid | 0.025 |
| GMS | 0.010 |
| Cetyl Alcohol | 0.100 |
| Silicone 350 | 0.002 |
| Propylparaben | 0.001 |
| Glycerin | 0.070 |
| Trolamine | 0.010 |
| Germall | 0.005 |
| Methylparaben | 0.002 |
| Carbomer 934 | 0.001 |
| Shea Butter | 0.030 |
| Aloe Vera (200:1) | 0.050 |
| Vitamin A Lipomicron | 0.003 |
| Vitamin E Lipomicron | 0.003 |
| Water | 0.638 |
| Aqua Gel Base Total Per 5 Gallon gel base | 1.000 |
| CPC (0.04%) | 200 ml |
| Equine (special made) Plasma | 1000 ml |
| Vitamin C solution | 50 ml |
| Glycerol | 150 ml |
| Bovine Thrombin (CaCl$_2$) | 6,000 U |
| DI water | 200 mL |

Mix for 25 minutes

IV. DISEASE STATES AND INDICATIONS

The compositions described herein can be used in the treatment of chronic wound types resulting from several causes, including trauma wounds resulting from lacerations, burns, surgical or medical procedures, chronic wounds, pressure wounds, sacral lick, granuloma, otitis, corneal ulcers, ear infections, animal bites such as snake bites, insect bites or spider bites. In one embodiment, the compositions described herein can be used to treat lower equine limbs with chronic wounds.

V. METHODS OF TREATMENT

One or more of the compositions described herein can be used singly or in combination to treat a wound. In one example of a wound care system, the following protocol can be performed. It should be appreciated that the following method is illustrative and is not meant to be limiting. One or more of the treatments can be excluded, added, performed simultaneously or performed in a different order.

The wound can be debrided, sanitized and flushed with a first composition including a combination of *Aloe vera*, Vitamin C, and CPC. An amount of composition can be applied to ensure that the wound is covered and stays in contact with the wound bed for a period of time.

The wound can then be treated with a second composition to assist in the granulation of the wound up to the level of the skin. The second composition can include a tissue regenerator including freeze-dried or frozen fresh platelet concentrate or a concentrated solution of enriched, activated platelet-rich plasma (PRP). The second composition can be applied as a spray (aerosolized or pump spray). Once the granulation of the wound reaches the level of the skin the treatment can then be discontinued. The first composition can continue to be used during the use of the second composition, for example when checking under a bandage or other wound covering to assess the state of healing.

A third composition, such as in a cream or paste form, can then be applied to the wound, for example once an epithelial border of the wound bed forms. The third composition can accelerate migration across the wound bed, wound contraction and help to keep the wound moist. The third composition can provide cosmetic heal, for example, by maintaining natural hair color near and around the wound site. The wound treatment system can reduce or eliminates scarring. The third composition can include a combination of an *Aloe vera*/hydrogel base containing Vitamin C, Vitamin A, Vitamin E, and immunoglobulins. Depending upon the size of the wound, the treatment can be extended for a number of days including at least about 3, 4, 5, 6, 7, 10, 14 or more days. The wound can be treated at least once a day for the number of days or until adequate healing is achieved. In an embodiment, the wound care system is used to treat a wound for at least 5 days. In another embodiment, the wound care system is used to treat a wound for at least about 10, 15, 20, 25, 30, 35, 40, 45, 50, 75, 100, or 120 days.

It should be appreciated that the wound bed can be exposed or can be covered during one or more stages of the treatment such as with a bandage or other wound covering device. For example, the wound can be covered by a traditional bandage during the time-frame of treatment with the first and second composition. Upon inspection of the wound under the bandage, the first composition can be used to sanitize the wound prior to application of the second composition and re-covering with a bandage. Generally, during treatment with the third composition the wound is left uncovered by a traditional bandage.

Conventional bandages of the lower leg, chest, neck and head wounds in large animals can be difficult to apply. Heavy bandaging of certain wounds, in particular equine lower leg wounds, can cause over-granulation of tissue at the wound site. The spray application of the compositions described herein allows a user to apply the composition without having to touch a wound or bandage it.

In one embodiment, the composition is delivered using a pump spray or an aerosol canister containing a nitrogen propellant. In each, the composition formula includes freeze-dried growth factor soup (GFS), ascorbic acid solution (50 g in 200 mL deionized water), and 0.04% CPC. The formula can also include glycerol and a starch solution between at least about 0.6% to about 1.0%. The starch solution can act as a carrier for the growth factors in the GFS such that they can bind their receptors in tissues at the wound bed as well as promote the accumulation of fluid and production of other growth factors that further promote wound healing. The ascorbic acid solution can aid in scavenging the free radicals within the wound bed causing a reduction in inflammation. The glycerol base can improve absorption within the fatty tissues of the wound bed and prevent the hydrophilic components of the composition from running off the wound.

In one method of use, for example in a large animal such as a horse, the wound can be cleaned in a warm saline solution to wash off any contaminants. The wound can be patted dry such as with a clean, dry terry cloth towel. A first composition containing *Aloe vera*, vitamin C, and CPC as described above can be used to flush and sanitize the wound to eliminate as many microbial organisms as possible. A second composition containing the freeze-dried GFS, ascorbic acid, and CPC in a glycerol starch solution can then be applied to the wound as a spray. For example, the nozzle can be held a distance from the wound, such as approximately 6-8 inches, while the wound is sprayed starting from the top, and moving side-to-side until completely covered with the composition. The wound coated with the second composition can then be covered, for example with a heavy, double-strength paper towel, and allowed to dry. The covering can prevent stall shavings and other contaminants from collecting on the treated wound. After a period of time, for example three days, the covering can be removed using a warm saline bath. The wound can be observed for the presence of an epithelial border and can then undergo continued treatment with a third composition such as the finishing composition described above containing *Aloe vera* gel, ascorbic acid, vitamin A, vitamin E and immunoglobulins.

VI. EXAMPLES

Example 1

Phenol Red Dextrose broth tubes were prepared and a small loop of an organism cultured in peptone broth for 24 hours at 37° C. was used to inoculate the tubes in duplicate to a series of ten. Product containing CPC was added in 0.1 mL increments to each of the inoculated tubes to cover a range of 0.1 to 1.0 mL. The inoculated tubes were incubated at a temperature of 37° C. for 24 hours and growth of organism assessed compared to an inoculated tube without presence of product. The positive control exhibited color change from red to yellow indicating positive growth whereas the negative control without an inoculation had no color change. Concentrations of cetyl pyridinium chloride (CPC) in the wound solution were tested to assess the minimum level of CPC required to kill a test organism and the results are shown in Table 4 below. The lowest concentration of CPC (0.1 ml CPC or 0.004% volume of composition) successfully killed all organisms tested.

TABLE 4

| | Organism | | | | | | |
|---|---|---|---|---|---|---|---|
| Treatment | Staph aureus (MRSA) | Staph aureus (non MRSA) | Strep pyogenes | Strep equi | Candida albicans | Proteus vulgaris | P. aeruginosa |
| 0.1 mL CPC (0.004% vol. comp) | n/g | n/g | n/g | n/g | n/g | n/g | n/g |
| 0.2 mL CPC (0.008% vol. comp) | n/g | n/g | n/g | n/g | n/g | n/g | n/g |
| 0.3 mL CPC (0.016% vol. comp) | n/g | n/g | n/g | n/g | n/g | n/g | n/g |

TABLE 4-continued

| Treatment | Staph aureus (MRSA) | Staph aureus (non MRSA) | Strep pyogenes | Strep equi | Candida albicans | Proteus vulgaris | P. aeruginosa |
|---|---|---|---|---|---|---|---|
| 0.4 mL CPC (0.032% vol. comp) | n/g | n/g | n/g | n/g | n/g | n/g | n/g |
| 0.5 mL CPC (0.064% vol. comp) | n/g | n/g | n/g | n/g | n/g | n/g | n/g |
| 0.6 mL CPC (0.128% vol. comp) | n/g | n/g | n/g | n/g | n/g | n/g | n/g |
| 0.7 mL CPC (0.256% vol. comp) | n/g | n/g | n/g | n/g | n/g | n/g | n/g |
| 0.8 mL CPC (0.512% vol. comp) | n/g | n/g | n/g | n/g | n/g | n/g | n/g |
| 0.9 mL CPC (1.024% vol. comp) | n/g | n/g | n/g | n/g | n/g | n/g | n/g |
| 1.0 mL CPC (2.048% vol. comp) | n/g | n/g | n/g | n/g | n/g | n/g | n/g | n/g—no growth of organism in 10 mL phenol Red Dextrose broth
CPC—cetyl pyridinium chloride While this specification contains many specifics, these should not be construed as limitations on the scope of what is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed.

What is claimed is:

1. A kit for treating a wound comprising:
 a first composition comprising: cetylpyridinium chloride, *Aloe vera*, and ascorbic acid for sanitizing a wound, wherein the cetylpyridinium chloride is at least about 0.2% by weight per volume of the first composition, wherein the *Aloe vera* is about 40:1 whole leaf to about 200:1 whole leaf and is at least about 0.5% by weight per volume of the first composition, and wherein the ascorbic acid is about 0.5% by weight per volume of the first composition;
 a second composition comprising: reconstituted concentrated, cytokine-rich freeze-dried plasma for activating granulation of the wound;
 a third composition comprising: *Aloe vera*, ascorbic acid, vitamin A, vitamin E and a source of immunoglobulins for initiating re-epithelialization of the wound; and
 a treatment protocol for applying to the wound a combination of the first composition, the second composition and the third composition according to and depending upon the phase of wound healing.

2. The kit of claim 1, wherein the first composition is in liquid form.

3. The kit of claim 2, wherein the liquid form of the first composition is a shampoo, pump spray, or an aerosol spray.

4. The kit of claim 1, wherein the second composition is in a fresh frozen or freeze-dried form and reconstituted with sterile deionized water prior to application to the wound.

5. The kit of claim 1, wherein the second composition activates granulation of the wound up to a level of a skin surface surrounding the wound.

6. The kit of claim 1, wherein the third composition is in a gel or solid form.

7. The kit of claim 6, wherein the third composition is applied using a squeeze tube or stick.

8. The kit of claim 1, wherein the third composition does not alter natural hair color at and around the wound.

9. The kit of claim 1, wherein the third composition accelerates migration across the wound, wound contraction, and keeps the wound moist.

10. The kit of claim 1, wherein the wound is on a mammal and the mammal is a primate.

11. The kit of claim 1, wherein the wound is on a mammal and the mammal is a non-primate.

12. The kit of claim 1, wherein the concentrated plasma is prepared from autologous blood.

13. The kit of claim 1, wherein the concentrated plasma is prepared from heterologous blood.

14. The kit of claim 12, wherein the wound is on a mammal, and the heterologous blood is from a species other than the species of the mammal.

15. The kit of claim 1, wherein the wound is an injury of a bodily tissue selected from the group consisting of skin, muscle, bone, cartilage, collagen, connective tissue, adipose, mucus membrane, cornea, ear and other tissues and parts of the body.

16. The kit of claim 15, wherein the injury is a puncture, laceration, surgical incision, chronic wound, pressure wound, open abscess, sacral lick, granuloma, abrasion, burn, otitis, corneal ulcer, ear infection, snake bite or spider bite.

17. The kit of claim 1, wherein the wound is a chronic wound of an equine lower limb.

18. The kit of claim 1, further comprising a wound cover.

19. The kit of claim 1, wherein the treatment protocol contains directions for applying the first, second and third compositions separately and sequentially according to and depending upon the phase of wound healing.

20. The kit of claim 1, wherein the treatment protocol contains directions for applying the first composition prior to the second composition and applying the second composition prior to the third composition.

21. The kit of claim 1, wherein the treatment protocol contains directions for applying the first composition one or more times a day for at least 5 days.

22. The kit of claim 1, wherein the treatment protocol contains directions for applying the second composition until granulation of the wound is up to the level of a skin surface surrounding the wound.

23. The kit of claim 1, wherein the treatment protocol contains directions for applying the third composition once an epithelial border of the wound forms.

24. The kit of claim 1, wherein the second composition is formulated as a freeze-dried aerosol spray.

25. The kit of claim 1, wherein the *Aloe vera* in the first composition is about 200:1 whole leaf and is at least about 0.5% by weight per volume of the first composition.

26. The kit of claim 25, wherein the *Aloe vera*, Vitamin A, and Vitamin E of the third composition is a gel base comprising about 200:1 *Aloe vera* gel that is about 5% volume per volume of the gel base, Vitamin A lipomicron that is about 0.3% volume per volume of the gel base, and Vitamin E lipomicron that is about 0.3% volume per volume of the gel base.

27. The kit of claim 26, wherein the ascorbic acid of the third composition is L-ascorbic acid USP that is about 0.26% weight per volume of the third composition.

* * * * *